United States Patent
Lilliestråle et al.

(10) Patent No.: US 11,645,749 B2
(45) Date of Patent: *May 9, 2023

(54) DETERMINATION AND VISUALIZATION OF DAMAGE TO AN ANATOMICAL JOINT

(71) Applicant: Episurf IP-Management AB, Stockholm (SE)

(72) Inventors: Richard Lilliestråle, Stockholm (SE); Anders Karlsson, Kävlinge (SE); Jeanette Spångberg, Skogås (SE); Nina Bake, Lidingö (SE); Ingrid Bratt, Solna (SE)

(73) Assignee: Episurf IP-Management AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/568,699

(22) Filed: Jan. 4, 2022

(65) Prior Publication Data

US 2022/0130042 A1 Apr. 28, 2022

Related U.S. Application Data

(63) Continuation of application No. 16/221,287, filed on Dec. 14, 2018, now Pat. No. 11,250,561.

(51) Int. Cl.
*G06T 7/00* (2017.01)
*A61B 34/10* (2016.01)
(Continued)

(52) U.S. Cl.
CPC .......... *G06T 7/0012* (2013.01); *A61B 6/032* (2013.01); *A61B 6/466* (2013.01); *A61B 6/50* (2013.01);
(Continued)

(58) Field of Classification Search
CPC ... A61B 6/466; A61B 34/10; A61B 2034/105; A61B 2034/107; G06T 15/00
See application file for complete search history.

(56) References Cited

U.S. PATENT DOCUMENTS 7,468,075 B2 12/2008 Lang et al.
7,664,297 B2 2/2010 Harada et al.
(Continued)

FOREIGN PATENT DOCUMENTS

CN 105997307 A 10/2016
CN 106132354 A 11/2016
(Continued)

OTHER PUBLICATIONS

Cohen et al., "Templates of the cartilage layers of the patellofemoral joint and their use in the assessment of osteoarthritic cartilage damage", Osteoarthritis and Cartilage 11(8):569-579, Aug. 2003.
(Continued)

*Primary Examiner* — Jason M Ip
(74) *Attorney, Agent, or Firm* — Davis Wright Tremaine LLP

(57) ABSTRACT

A system for determining and visualizing damage to an anatomical joint of a patient. The system is to: obtain a three dimensional image representation of an anatomical joint which is based on a medical image stack; determine damage to an anatomical structure in the anatomical joint by analyzing the medical image stack; mark damage to the anatomical structures in the obtained three dimensional image representation; obtain a 3D model based on the three dimensional image representation; and create a graphical user interface (GUI). The GUI may comprise: functionality to visualize and enable manipulation of the at least one 3D model; functionality to enable removal of the visualization of the anatomical structure from the 3D model; functionality to visualize and enable browsing of the medical image stack;
(Continued)

and functionality to visualize the position of the medical image that is currently visualized.

12 Claims, 8 Drawing Sheets

(51) Int. Cl.

| | | |
|---|---|---|
| *G06T 15/00* | (2011.01) | |
| *A61B 6/00* | (2006.01) | |
| *G06T 17/00* | (2006.01) | |
| *G06T 19/20* | (2011.01) | |
| *A61B 6/03* | (2006.01) | |

(52) U.S. Cl.
CPC ............ *A61B 6/5217* (2013.01); *A61B 34/10* (2016.02); *G06T 15/00* (2013.01); *G06T 17/00* (2013.01); *G06T 19/20* (2013.01); *A61B 2034/105* (2016.02); *A61B 2034/107* (2016.02); *A61B 2034/108* (2016.02); *G06T 2207/10081* (2013.01); *G06T 2207/30008* (2013.01); *G06T 2219/028* (2013.01)

(56) References Cited

U.S. PATENT DOCUMENTS

| | | |
|---|---|---|
| 8,657,827 B2 | 2/2014 | Fitz et al. |
| 2002/0087274 A1 | 7/2002 | Alexander et al. |
| 2002/0147392 A1 | 10/2002 | Steines et al. |
| 2002/0177770 A1 | 11/2002 | Lang et al. |
| 2003/0216669 A1 | 11/2003 | Lang et al. |
| 2004/0147927 A1 | 7/2004 | Tsougarakis et al. |
| 2004/0153079 A1 | 8/2004 | Tsougarakis et al. |
| 2004/0167390 A1 | 8/2004 | Alexander et al. |
| 2005/0049524 A1 | 3/2005 | Lefevre et al. |
| 2005/0054917 A1 | 3/2005 | Kitson |
| 2005/0102315 A1 | 5/2005 | Krishnan |
| 2007/0015995 A1 | 1/2007 | Lang et al. |
| 2007/0203430 A1 | 8/2007 | Lang et al. |
| 2007/0276224 A1 | 11/2007 | Lang et al. |
| 2008/0015433 A1 | 1/2008 | Alexander et al. |
| 2008/0195216 A1 | 8/2008 | Philipp |
| 2008/0232658 A1 | 9/2008 | Sugaya et al. |
| 2009/0076371 A1 | 3/2009 | Lang et al. |
| 2009/0157083 A1 | 6/2009 | Park et al. |
| 2009/0268956 A1 | 10/2009 | Wiley |
| 2009/0270868 A1 | 10/2009 | Park et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0111837 A1 | 5/2010 | Boyden et al. |
| 2010/0256479 A1 | 10/2010 | Park et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305907 A1 | 12/2010 | Fitz et al. |
| 2010/0329530 A1 | 12/2010 | Lang et al. |
| 2011/0009964 A1 | 1/2011 | Schwartz et al. |
| 2011/0054486 A1 | 3/2011 | Linder-Ganz et al. |
| 2011/0087465 A1 | 4/2011 | Mahfouz |
| 2011/0125003 A1 | 5/2011 | Reach |
| 2011/0125009 A1 | 5/2011 | Lang et al. |
| 2011/0214279 A1 | 9/2011 | Park et al. |
| 2011/0282473 A1 | 11/2011 | Pavlovskaia et al. |
| 2011/0295329 A1 | 12/2011 | Fitz et al. |
| 2011/0295378 A1 | 12/2011 | Bojarski et al. |
| 2012/0072183 A1 | 3/2012 | Lang et al. |
| 2012/0143197 A1 | 6/2012 | Lang et al. |
| 2012/0209394 A1 | 8/2012 | Bojarski et al. |
| 2012/0232670 A1 | 9/2012 | Bojarski et al. |
| 2012/0265496 A1 | 10/2012 | Mahfouz |
| 2012/0310347 A1 | 12/2012 | Linder-Ganz et al. |
| 2012/0310400 A1 | 12/2012 | Park et al. |
| 2013/0006598 A1 | 1/2013 | Alexander et al. |
| 2013/0035561 A1 | 2/2013 | Sharkey et al. |
| 2013/0071828 A1 | 3/2013 | Lang et al. |
| 2013/0110252 A1 | 5/2013 | Bake et al. |
| 2013/0116788 A1 | 5/2013 | Schwartz et al. |
| 2013/0123789 A1 | 5/2013 | Park |
| 2013/0137962 A1 | 5/2013 | Urish et al. |
| 2013/0173228 A1 | 7/2013 | Bake et al. |
| 2013/0184820 A1 | 7/2013 | Schwartz et al. |
| 2013/0185927 A1 | 7/2013 | Bake et al. |
| 2013/0211232 A1 | 8/2013 | Murphy et al. |
| 2013/0336553 A1 | 12/2013 | Buisseret et al. |
| 2013/0345845 A1 | 12/2013 | Park et al. |
| 2014/0005792 A1 | 1/2014 | Lang et al. |
| 2014/0005997 A1 | 1/2014 | Park et al. |
| 2014/0029814 A1 | 1/2014 | Fitz et al. |
| 2014/0039454 A1 | 2/2014 | Sharkey |
| 2014/0078139 A1 | 3/2014 | Park et al. |
| 2014/0142643 A1 | 5/2014 | Bake et al. |
| 2014/0249627 A1 | 9/2014 | Linder-Ganz et al. |
| 2014/0257508 A1 | 9/2014 | Bojarski et al. |
| 2014/0378978 A1 | 12/2014 | Park |
| 2015/0120031 A1 | 4/2015 | Mahfouz |
| 2015/0260819 A1 | 9/2015 | Lauer et al. |
| 2015/0327795 A1 | 11/2015 | Alexander et al. |
| 2015/0342739 A1 | 12/2015 | Mahfouz |
| 2016/0000571 A1 | 1/2016 | Mahfouz |
| 2016/0038248 A1 | 2/2016 | Bharadwaj et al. |
| 2016/0045317 A1 | 2/2016 | Lang et al. |
| 2016/0199075 A1 | 7/2016 | Bake |
| 2016/0228194 A1 | 8/2016 | Park et al. |
| 2016/0228195 A1 | 8/2016 | Park et al. |
| 2016/0228196 A1 | 8/2016 | Park et al. |
| 2016/0228197 A1 | 8/2016 | Park et al. |
| 2016/0270696 A1 | 9/2016 | Lang et al. |
| 2016/0270856 A1 | 9/2016 | Park et al. |
| 2016/0270857 A1 | 9/2016 | Park et al. |
| 2016/0270858 A1 | 9/2016 | Park et al. |
| 2016/0270859 A1 | 9/2016 | Park et al. |
| 2016/0335776 A1 | 11/2016 | Maes et al. |
| 2016/0354092 A1 | 12/2016 | Park |
| 2016/0364862 A1 | 12/2016 | Reicher et al. |
| 2017/0000569 A1 | 1/2017 | Mahfouz |
| 2017/0000614 A1 | 1/2017 | Mahfouz |
| 2017/0000615 A1 | 1/2017 | Mahfouz |
| 2017/0027701 A1 | 2/2017 | Mahfouz |
| 2017/0100253 A1 | 4/2017 | Bake et al. |
| 2017/0135769 A1 | 5/2017 | Karlsson et al. |
| 2017/0172747 A1 | 6/2017 | Bake et al. |
| 2017/0273745 A1 | 9/2017 | Turquier et al. |
| 2018/0185038 A1 | 7/2018 | Hero et al. |

FOREIGN PATENT DOCUMENTS

| | | |
|---|---|---|
| EP | 1139872 A2 | 10/2001 |
| EP | 1319217 A2 | 6/2003 |
| EP | 1322224 A1 | 7/2003 |
| EP | 1322225 A1 | 7/2003 |
| EP | 1389980 A2 | 2/2004 |
| EP | 1406203 A2 | 4/2004 |
| EP | 1450696 A1 | 9/2004 |
| EP | 1208410 B1 | 12/2004 |
| EP | 1558181 A1 | 8/2005 |
| EP | 2036495 A1 | 3/2009 |
| EP | 2114312 A2 | 11/2009 |
| EP | 2280671 A1 | 2/2011 |
| EP | 2291147 A1 | 3/2011 |
| EP | 2304645 A2 | 4/2011 |
| EP | 2319450 A1 | 5/2011 |
| EP | 2339991 A1 | 7/2011 |
| EP | 2389899 A1 | 11/2011 |
| EP | 2389905 A1 | 11/2011 |
| EP | 2400921 A1 | 1/2012 |
| EP | 2405865 A2 | 1/2012 |
| EP | 2470115 A1 | 7/2012 |
| EP | 2591756 A1 | 5/2013 |
| EP | 2765955 A1 | 8/2014 |
| EP | 3013256 A1 | 5/2016 |
| EP | 3075356 A1 | 10/2016 |

(56) References Cited

FOREIGN PATENT DOCUMENTS

| | | |
|---|---|---|
| EP | 2967813 A4 | 11/2016 |
| EP | 3102154 A1 | 12/2016 |
| EP | 3181050 A1 | 6/2017 |
| JP | H11104072 A | 4/1999 |
| JP | 2002532126 A | 10/2002 |
| JP | 2003144454 A | 5/2003 |
| JP | 2007268275 A | 10/2007 |
| JP | 2008093229 A | 4/2008 |
| JP | 2010503503 A | 2/2010 |
| JP | 2010264230 A | 11/2010 |
| JP | 2014000425 A | 1/2014 |
| JP | 2014516630 A | 7/2014 |
| JP | 2017510307 A | 4/2017 |
| WO | 0035346 A2 | 6/2000 |
| WO | 0222013 A1 | 3/2002 |
| WO | 0222014 A1 | 3/2002 |
| WO | 0223483 A2 | 3/2002 |
| WO | 32087444 A1 | 11/2002 |
| WO | 02096268 A2 | 12/2002 |
| WO | 03039377 A1 | 5/2003 |
| WO | 2004043305 A1 | 5/2004 |
| WO | 2008101090 A2 | 8/2008 |
| WO | 2009154691 A2 | 12/2009 |
| WO | 2010099231 A2 | 9/2010 |
| WO | 2010099359 A1 | 9/2010 |
| WO | 2010099360 A1 | 9/2010 |
| WO | 2011147832 A1 | 12/2011 |
| WO | 2011147837 A1 | 12/2011 |
| WO | 2012143628 A1 | 10/2012 |
| WO | 2013052767 A1 | 4/2013 |
| WO | 2013056036 A1 | 4/2013 |
| WO | 2014145267 A1 | 9/2014 |
| WO | 2014206498 A1 | 12/2014 |
| WO | 2014207151 A1 | 12/2014 |
| WO | 2015117663 A1 | 8/2015 |
| WO | 2016004991 A1 | 1/2016 |
| WO | 2016004992 A1 | 1/2016 |
| WO | 2016005541 A1 | 1/2016 |
| WO | 2016005542 A1 | 1/2016 |
| WO | 2017103146 A1 | 6/2017 |

OTHER PUBLICATIONS

Dodin et al., "A fully automated system for quantification of knee bone marrow lesions using MRI and the osteoarthrtis initiative cohort," Journal of Biomedical Graphics and Computing 3(1):51-65, Dec. 17, 2012, doi:10.5430/jbgc.v3n1p51.

Extended European Search Report dated Oct. 4, 2017, issued in EP Patent Application No. 17176394.9, filed Dec. 18, 2015, 10 pages.

Nielsen et al., "Measurement of bone marrow lesions by MR imaging in knee osteoarthritis using quantitative segmentation methods—a reliability and sensitivity to change analysis," BMC Musculoskeletal Disorders 15(447), Dec. 20, 2014, 11 pages, doi:10.1186/1471-2474-15-447.

Birr et al., "The LiverAnatomyExplorer: A WebGL-Based Surgical Teaching Tool," IEEE Computer Graphics and Applications 33(5):48-58, published online May 2, 2013, print publication Sep. 1, 2013.

Mühler et al., "The Medical Exploration Toolkit: An Efficient Support for Visual Computing in Surgical Planning and Training", IEEE Transactions on Visualization and Computer Graphics 16(1):133-146, Jan. 1, 2010.

International Search Report and Written Opinion dated Jul. 26, 2018, International Patent Application No. PCT/EP2018/066012, filed Jun. 15, 2018, 14 pages.

Japanese Notice of Reasons for Refusal dated Jun. 25, 2019, Patent Application No. 2018-525771, filed Dec. 16, 2016, 5 pages.

International Search Report and Written Opinion dated Sep. 16, 2019, Patent Application No. PCT/EP2018/085055, filed Dec. 14, 2018, 14 pages.

Japanese Office Action dated Jan. 26, 2021, Patent Application No. 2019-561189, 6 pages.

Ramakrishna et al., "An Automatic Computer-Aided Detection System for Meniscal Tears on Magnetic Resonance Images," IEEE Transactions on Medical Imaging 28(8):1308-16, Feb. 20, 2009.

Taiwan Patent Office, "Examination Report" in application No. 107120781 dated Oct. 19, 2022, 12 pages.

DETERMINATION AND VISUALIZATION OF DAMAGE TO AN ANATOMICAL JOINT

CROSS-REFERENCE TO RELATED APPLICATIONS

This application is a continuation of U.S. application Ser. No. 16/221,287, filed Dec. 14, 2018, entitled "DETERMINATION AND VISUALIZATION OF DAMAGE TO AN ANATOMICAL JOINT," which incorporates by reference U.S. application Ser. No. 16/010,344, filed Jun. 15, 2018, entitled "CREATION OF A DECISION SUPPORT MATERIAL INDICATING DAMAGE TO AN ANATOMICAL JOINT," and U.S. application Ser. No. 15/625,873, filed Jun. 16, 2017, entitled "SYSTEM AND METHOD FOR CREATING A DECISION SUPPORT MATERIAL INDICATING DAMAGE TO AN ANATOMICAL JOINT" and further incorporates by reference for all purposes the full disclosure of PCT Application No. PCT/EP2018/066012, filed on Dec. 20, 2018, entitled "CREATION OF A DECISION SUPPORT MATERIAL INDICATING DAMAGE TO AN ANATOMICAL JOINT," and co-pending U.S. patent application Ser. No. 15/611,685, filed Jun. 1, 2017, entitled "SYSTEM AND METHOD FOR CREATING A DECISION SUPPORT MATERIAL INDICATING DAMAGE TO AN ANATOMICAL JOINT," which is a continuation of U.S. patent application Ser. No. 15/382,523, filed Dec. 16, 2016, entitled "SYSTEM AND METHOD FOR CREATING A DECISION SUPPORT MATERIAL INDICATING DAMAGE TO AN ANATOMICAL JOINT," which claims benefit of EP Application No. 15201361.1, filed Dec. 18, 2015, the content of which are incorporated by reference herein in their entirety.

TECHNICAL FIELD

The present disclosure relates generally to systems and methods for determining and visualizing damage to an anatomical joint of a patient.

BACKGROUND

It is important for medical personnel to be able to determine damage to an anatomical joint, so that a suitable treatment may be proposed.

In order to determine damage to an anatomical joint, it is common in medical practice to use imaging techniques to depict the anatomical joint of interest and then have a medical expert analyze the captured image data to determine whether there is damage. The medical expert makes annotations about the conclusions drawn from the analysis of image data, that are made available to a surgeon or orthopedic staff member who uses the annotations and the captured image data as a decision support for diagnosis and decision of suitable treatment of the patient.

However, this process is not very efficient as a manner of providing decision support, as only a fraction of the information that the medical expert in this way gathers when analyzing the image data, based on the knowledge of the medical expert, can be communicated in the present annotation format. Therefore, the decision support material received by the surgeon or orthopedic staff member is often inadequate.

Steven Birr et al: "The LiverAnatomyExplorer", IEEE Computer Graphics and Applications, vol. 33, issue 5 (September/October 2013), page 48-58, describes an anatomical and surgical teaching tool for 3D visualizations of the human anatomy. In the tool, 2D and 3D viewers are placed side by side, and the slice's position in the 2D viewer is visualized in the 3D model.

Problems with the Prior Art

The tool described in "The LiverAnatomyExplorer" is a teaching tool for visualizing organs. This tool does not comprise manipulation functionalities that enable the creation of a clear visualization of anatomical structures of an anatomical joint.

There is a need to address these problems of conventional methods and systems.

SUMMARY

A system that determines damage to an anatomical joint and visualizes this determined damage would be very useful as decision support.

The above described problems are addressed by the claimed system for determining and visualizing damage to an anatomical joint of a patient. The system may comprise a display, at least one manipulation tool, a storage media and at least one processor. The at least one processor may be configured to: i) receive a plurality of medical image stacks of at least a part of the anatomical joint from the storage media; ii) obtain a three-dimensional image representation of the at least part of the anatomical joint which is based on at least one of said medical image stacks, by generating said three-dimensional image representation in an image segmentation process based on said medical image stack, or receiving said three-dimensional image representation from the storage media; iii) determine damage to at least one of a plurality of anatomical structures in the anatomical joint by analyzing at least one of said plurality of medical image stacks; iv) mark, based on the determined damage, damage to the anatomical structures in the obtained three-dimensional image representation; v) obtain at least one 3D model for visualization based on the three-dimensional image representation, in which 3D model the marked damage is visualized; and vi) create a graphical user interface for visualization on the display. The graphical user interface may comprise: functionality to visualize and enable manipulation, using the at least one manipulation tool, of the at least one 3D model; functionality to enable removal of the visualization of at least one of the plurality of anatomical structures from the at least one 3D model; functionality to visualize and enable browsing of at least one of the plurality of medical image stacks; and functionality to, in the 3D model, visualize the position of the at least one medical image that is currently visualized.

In embodiments, the at least one processor is further configured to associate the medical images and the three-dimensional image representation, so that a marking made in one of the images appears in the same position in the other image.

The above described problems are also addressed by the claimed method for determining and visualizing damage to an anatomical joint of a patient. The method may comprise the steps of: i) receiving a plurality of medical image stacks of at least a part of the anatomical joint; ii) obtaining a three-dimensional image representation of the at least part of the anatomical joint which is based on at least one of said medical image stacks, by generating said three-dimensional image representation in an image segmentation process based on said medical image stack, or receiving said three-dimensional image representation from a storage media; iii)

determining damage to at least one of a plurality of anatomical structures in the anatomical joint by analyzing at least one of said plurality of medical image stacks; iv) marking, based on the determined damage, damage to the anatomical structures in the obtained three-dimensional image representation; v) obtaining at least one 3D model based on the three-dimensional image representation, in which 3D model the marked damage is visualized; and vi) creating a graphical user interface for visualization on a display. The graphical user interface may comprise: functionality to visualize and enable manipulation, using at least one manipulation tool, of the at least one 3D model; functionality to enable removal of the visualization of at least one of the plurality of anatomical structures from the at least one 3D model; functionality to visualize and enable browsing of at least one of the plurality of medical image stacks; and functionality to, in the 3D model, visualize the position of the at least one medical image that is currently visualized.

In embodiments, the method further comprises associating the medical images and the three-dimensional image representation, so that a marking made in one of the images appears in the same position in the other image.

In embodiments of the above described systems and methods, the plurality of anatomical structures are anatomical structures of the knee joint, such as e.g. a selection of femur, patella, tibia, fibula, cartilage, menisci, cruciate ligaments and tendons. The plurality of anatomical structures may alternatively comprise a different selection of different parts of bone, cartilage, ligaments and/or tendons, especially if the anatomical joint is not a knee. The anatomical structures are preferably structures that are relevant to a user who uses the graphical user interface to evaluate the condition of an anatomical joint.

In embodiments of the above described systems and methods, a plurality of the anatomical structures is each visualized based on more than one computer file. An anatomical structure is not simply what is visualized using one computer file, but a structure that is of relevance to a user viewing and manipulating the 3D model in the graphical user interface. Many such anatomical structures are each visualized using a number of different computer files.

In embodiments of the above described systems and methods, the graphical user interface comprises functionality to select at least one medical image in the medical image stack to visualize through interaction with the 3D model.

In embodiments of the above described systems and methods, the graphical user interface comprises functionality to visualize a plurality of medical image stacks simultaneously, and functionality to visualize the position in the imaged joint of the at least one medical image from one medical image stack, that is currently visualized, in in the medical image that is visualized from the other medical image stack.

In embodiments of the above described systems and methods, the medical images are MR images, and the scanning process is an MR scanning process using a number of specific MR sequences, where each specific MR sequence uses a unique set of MR parameters.

In embodiments of the above described systems and methods, the medical images are CT images, and the scanning process is a CT scanning process using a number of specific CT sequences, where each specific CT sequence uses a unique set of CT parameters.

In the above described systems and methods, the image segmentation process may e.g. depend on a segmentation process control parameter set. The anatomical joint may be a knee, but may also be another joint such as an ankle, a hip, a toe, an elbow, a shoulder, a finger or a wrist. The graphical user interface may e.g. be adapted to be used by medical staff. It may include a recommendation for a suitable treatment for repair of the determined damage.

The above described problems are also addressed by a non-transitory machine-readable medium on which is stored machine-readable code which, when executed by a processor, controls the processor to perform any one of the above described methods.

The processor may in some embodiments comprise several different processors which together perform the claimed functions. In the same way, the storage media may in some embodiments comprise several different storage media which together perform the claimed functions.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Introduction

Figure 1:
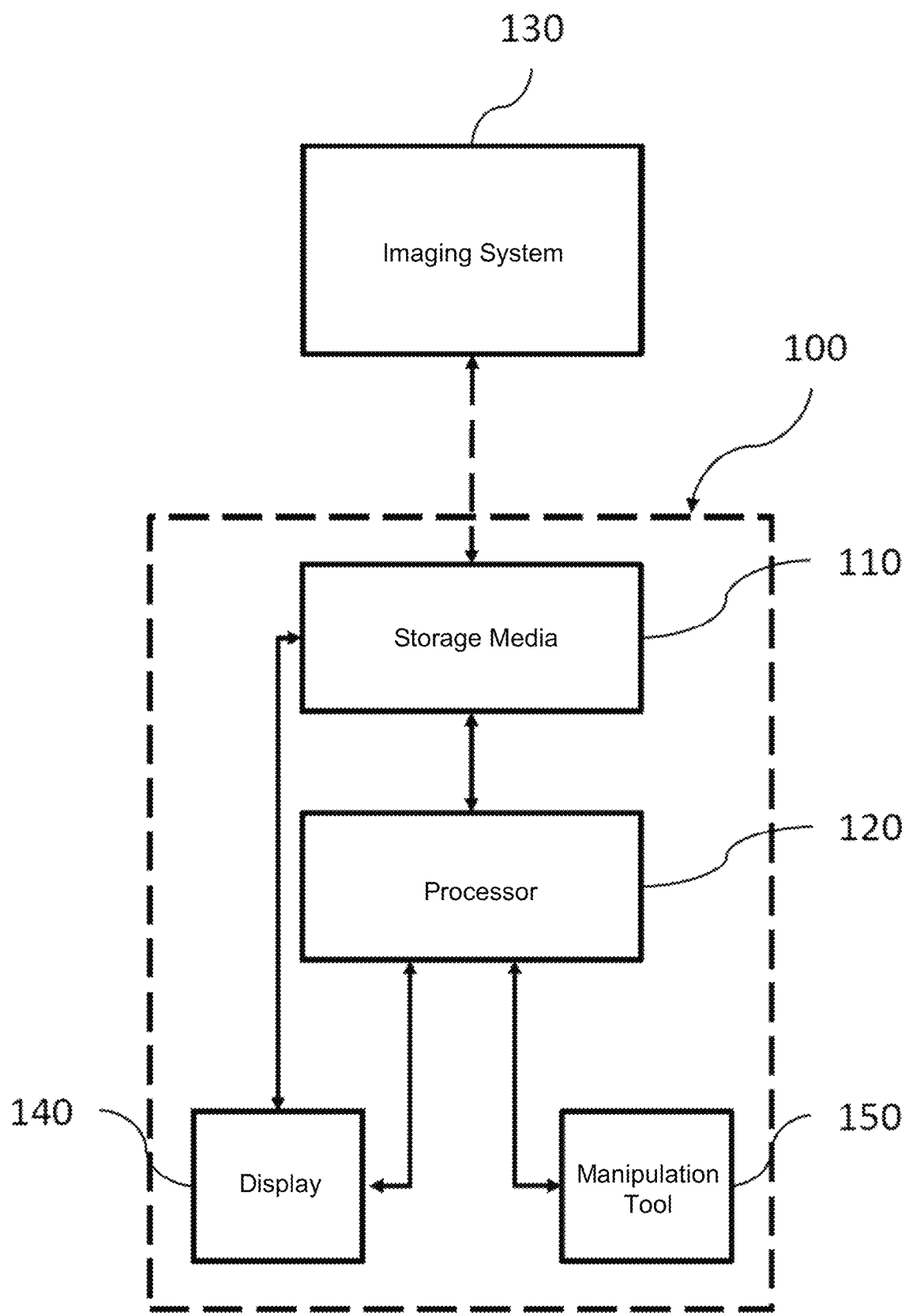
FIG. 1 shows a schematic view of a system for determining and visualizing damage to at least a part of an anatomical joint, in accordance with one or more embodiments described herein.

The present disclosure relates generally to systems and methods for determining and visualizing damage to an anatomical joint of a patient.

More specifically, system and method embodiments presented herein provide visualization of damage to an anatomical joint of a patient by creating a graphical user interface in which damage to an anatomical joint of a patient is visualized. In other words, there is provided one or more visualizations of a patient's joint together with a visualization of its anatomical deviations, which form a decision support for a surgeon or orthopedic staff member in deciding on an optimal treatment method, a decision support for an insurance agent making an assessment regarding a client or potential client, a decision support for a patient who wants to be informed about the condition of a damaged joint, or a decision support for any other person who has for example a commercial or academic interest in learning about damage to a depicted anatomical joint. This provides great advantages compared to conventional systems and methods, as much more information obtained from the medical image data is communicated, for example to the person making the decision on treatment of the patient. Thereby, embodiments of the invention solve the identified problems that the decision support material received by the surgeon or orthopedic staff member is many times inadequate as only a fraction of the information that a medical expert gathers when analyzing the image data, based on the knowledge of the medical expert, is communicated. In other words, using embodiments presented herein, a graphical user interface for visualization of damage to an anatomical joint of a patient is obtained, which leads to more informed decisions being made on the optimal treatment of the patient whose anatomical joint is visualized.

In some embodiments, the anatomical joint is a knee, but the methods and systems presented herein may be used for visualizing damage to any suitable anatomical joint, e.g. an ankle, a hip, a toe, an elbow, a shoulder, a finger or a wrist. The visualization need not relate to a whole anatomical joint—often only a part of the joint is of interest, such as e.g. the femoral part of the knee joint.

In a non-limiting example, the anatomical joint is a knee and the damage/anatomical deviations that are determined and visualized in the graphical user interface are related to the femoral part of the knee joint, such as chondral and/or osteochondral lesions. In another non-limiting example, the anatomical joint is an ankle and the damage/anatomical deviations that are determined and visualized in the graphical user interface are related to the talus.

The graphical user interface may comprise at least one 3D model of the anatomical joint and medical image data retrieved directly from a digital imaging and communications in medicine (DICOM) file or any other suitable image file format. The 3D model may for example be obtained based on a medical image stack captured during a process of scanning images through different layers of the anatomical joint or part of it.

Each medical image stack may e.g. be generated during a scanning process using a specific sequence, comprising a unique set of parameters that differs from the set of parameters used for generating the other medical image stacks. Such a scanning process may be any type of scanning process for generating medical image stacks, where different sets of parameters may be used to generate medical image stacks with different types of detail. The use of different specific sequences for different uses of the medical image stacks allows the visualization of more detail in the images, since some types of detail may be more clearly visible using one set of parameters and other types of detail may be more clearly visible using another set of parameters. It may e.g. be useful to use an adapted sequence in the scanning process for generating the medical image stack used for generating the 3D model, since the requirements on such a medical image stack are different from the requirements on the medical image stack used for damage determination.

The scanning processes used for generating the medical image stacks may e.g. be MR scanning processes using different specific MR sequences, where each specific MR sequence uses a unique set of MR parameters. The MR parameters may e.g. be the repetition time TR (the time between the RF pulses) and the echo time TE (the time between an RF pulse and its echo). Depending on the desired information, the set of MR parameters may e.g. cause a T1 weighted MR sequence if a short TR and a short TE is selected, a T2 weighted MR sequence if a long TR and a long TE is selected, or an intermediately weighted MR sequence of a long TR and a short TE is selected. The different sets of MR parameters do not necessarily have to cause MR sequences of different types—two different sets of MR parameters may e.g. both cause T1 weighted sequences, but one of the sets may cause a stronger T1 weighting than the other. There are also other MR parameters, such as e.g. flip angle, bandwidth or different types of fat suppression or enhancement of gadolinium, which may be varied between the MR sequences.

In MR scanning, it may be advantageous to use very different sets of MR parameters for generating the medical image stack used for generating the 3D model and for generating the other medical image stacks. It may e.g. be advantageous to use a specific 3D MRI sequence for generating the medical image stack used for generating the 3D model. In a 2D MRI sequence, each radiofrequency (RF) pulse excites a narrow slice, and magnetic field gradients are applied in two directions parallel to the plane in order to analyze the result. Such slices may then be combined into a 3D volume. In a 3D MRI sequence, on the other hand, each RF pulse excites the entire imaging volume, and magnetic field gradients are applied in three directions in order to analyze the result. In this way, a 3D volume may be created directly. Encoding (e.g. phase encoding) may be used to discriminate spatially.

The scanning processes used for generating the medical image stacks may also be CT scanning processes using different specific CT sequences, where each specific CT sequence uses a unique set of CT parameters. The CT parameters may e.g. be the tube potential (kV), the tube current (mA), the tube current product (mAs), the effective tube current-time product (mAs/slice), the tube current modulation (TCM), the table feed per rotation (pitch), the detector configuration, the collimation, the reconstruction algorithm, the patient positioning, the scan range and/or the reconstructed slice thickness. Also in CT scanning, it may be advantageous to use very different sets of CT parameters for generating the medical image stack used for generating the 3D model and for generating the other medical image stacks.

A 3D model is advantageous for visualizing damage to bone, cartilage and other tissues. The DICOM format, or a comparable medical image file format, is advantageous for visualizing different parts of the anatomical joint. For example, a 3D model may be used for visualizing anatomical structures such as different parts of bone, ligaments, tendons and/or cartilage, e.g. anatomical structures of the knee joint such as a selection of femur, patella, tibia, fibula, cartilage, menisci, cruciate ligaments and tendons, and damage in relation to the anatomical joint that is being investigated.

The graphical user interface may visualize a 3D model and at least one medical image to, for instance, facilitate for a surgeon or orthopedic staff member to make a correct diagnosis and decide on an optimal treatment of the patient. The graphical user interface does not include any diagnosis, but instead forms a decision support for making a correct diagnosis and/or decide on an optimal treatment of the patient. The graphical user interface may for instance be used as a pre-arthroscopic tool, a digital version of standard arthroscopy to be used prior to an arthroscopy to give an arthroscopist a visual understanding of what he/she can expect to see. The graphical user interface may also be used as an alternative to arthroscopy, since enough information can often be gathered in this way without submitting the patient to an arthroscopy. The graphical user interface may in this case be used as a tool for planning the preferred treatment, such as an arthroplasty, a biological treatment such as a mosaicplasty of a microfracturing, or if a metal implant is needed.

In other examples, other types of users may use the graphical user interface for different purposes. The graphical user interface may in different situations be of interest to medical staff, an insurance agent assessing a client or a potential client, a patient who wants to be informed about the condition of a damaged joint, or any other person who has for example a commercial or academic interest in learning about damage to a depicted anatomical joint. The graphical user interface is preferably web based.

A user who is viewing the graphical user interface on a display of a processing device may be allowed to manipulate the 3D model and/or the at least one medical image, by providing a control signal using at least one manipulation tool connected to the processing device. The manipulation tool may for example comprise a keyboard, a computer mouse, buttons, touch functionality, a joystick, or any other suitable manipulation tool.

In some embodiments, the graphical user interface may further include a recommendation and/or a position indication of a suitable implant for the determined damage. In this context, a suitable implant means an implant having a type and dimensions that match a determined damage, thereby making it suitable for repairing the determined damage. Such a suitable implant may further be visualized in the 3D model and/or the displayed medical image.

The graphical user interface may in some embodiments instead include a recommendation indicating a suitable transfer guide tool and/or suitable harvesting and/or implantation positions for at least one osteochondral autograft plug. The suitable transfer guide tool and/or the suitable harvesting and implantation positions may further be visualized in the 3D model and/or the displayed medical image.

In some embodiments, the graphical user interface further indicates anatomical deviations which do not in themselves constitute damage to the joint. Such anatomical deviations may e.g. affect the choice of treatment for the determined damage. As a non-limiting example, severe osteophyte problems may indicate other problems, where an implant may not improve the situation.

System and method embodiments of the disclosed solution are presented in more detail in connection with the figures.

System Architecture

FIG. 1 shows a schematic view of a system 100 for determining and visualizing damage to an anatomical joint of a patient. According to embodiments, the system comprises a display 140, at least one manipulation tool 150, and a storage media 110, configured to receive and store image data and parameters. In some embodiments, the system 100 is communicatively coupled, as indicated by the dashed arrow, to an imaging system 130. The imaging system 130 may be configured to capture or generate medical images, e.g. radiology images such as X-ray images, ultrasound images, computed tomography (CT) images, nuclear medicine including positron emission tomography (PET) images, and magnetic resonance imaging (Mill) images. The storage media 110 may be configured to receive and store medical images and/or medical/radiology image data from the imaging system 130.

The system 100 further comprises a processor 120 configured to, based on image data, determine damage to an anatomical joint, and create a 3D model of the anatomical joint or a part of it where the determined damage to the joint is visualized, such that an observer of the 3D model is made aware of the damage. The processor 120 may for example be a general data processor, or other circuit or integrated circuit capable of executing instructions to perform various processing operations. The display 140 may be configured to receive image data for display via the processor 120, and/or to retrieve image data for display directly from the storage media 110, possibly in response to a control signal received from the processor 120 or the at least one manipulation tool 150.

In one or more embodiments, the processor 120 is configured to: receive a plurality of medical image stacks of the at least part of the anatomical joint from the storage media 110; obtain a three-dimensional image representation of the at least part of the anatomical joint which is based on at least one of said of medical image stacks by generating said three-dimensional image representation in an image segmentation process based on said medical image stack, or receiving said three-dimensional image representation from the storage media 110; determine damage to at least one of a plurality of anatomical structures in the anatomical joint by analyzing at least one of said plurality of medical image stacks; mark, based on the determined damage, damage to the anatomical structures in the obtained three-dimensional image representation; obtain at least one 3D model based on the three-dimensional image representation, in which 3D model the marked damage is visualized; and create a graphical user interface for visualization on the display 140. The graphical user interface may comprise functionality to visualize and enable manipulation, using the at least one manipulation tool, of the at least one 3D model; functionality to enable removal of the visualization of at least one of the plurality of anatomical structures from the at least one 3D model; functionality to visualize and enable browsing of at least one of the plurality of medical image stacks; and functionality to, in the 3D model, visualize the position of the at least one medical image that is currently visualized.

In one or more embodiments the at least one processor 120 is configured to determine damage to at least one of a plurality of anatomical structures in the anatomical joint. The processor 120 may e.g. determine damage by detecting that the intensity in an area within or adjacent to the bone and/or cartilage parts of the anatomical joint is higher or lower than a predetermined threshold. Depending on the settings of the imaging device that has captured the analyzed medical image data, the analyzed image may for example represent the following substances with different intensity levels: cortical bone, fluid/liquids, cartilage, tendons, ligaments, fat/bone marrow and menisci. It is for example an indication of damage if fluid is detected where there in a healthy joint should be no fluid. If fluid is detected next to abnormalities in the cartilage, this can also be an indication of damage. Different intensity levels in the analyzed image correspond to different signal intensity levels, and these may typically be represented by pixel/voxel values ranging from 0 to 1, or in a visual representation shown as grey scale levels from white to black. In embodiments where the pixel/voxel values range from 0 to 1, a predetermined threshold is set to a suitable value between 0 and 1, or in other words to a suitable grey scale value.

In one or more embodiments the processor 120 may further, or alternatively, be configured to detect an irregular shape of at least one tissue part of the anatomical joint and determine whether this represents a damage to the anatomical joint. In one or more embodiments the processor 120 may further, or alternatively, be configured to make a comparison of an identified tissue part in a damage image with a template representing a predefined damage pattern for an anatomical joint. In some embodiments, such a determination may include comparing a detected irregular shape of the contour with a template representing a predefined damage pattern for an anatomical joint, and/or comparing a detected intensity for a certain area with a template representing a predefined damage pattern for an anatomical joint.

The at least one processor 120 may use a machine learning system in determining damage to the at least one of the plurality of anatomical structures in the anatomical joint. A machine learning system may e.g. be trained using images where damage has been manually marked, and may thereby learn to correlate different types of features and/or deviations in the images with damage.

In one or more embodiments, the processor 120 may be configured to mark the determined damage to the anatomical joint in the medical images. To mark the determined damage, the processor 120 may be configured to change the pixel/voxel value of one or more pixels/voxels on, in connection with, or surrounding a pixel/voxel identified to belong to a determined damage, such that the determined damage is visually distinguished and noticeable to a user/viewer, by performing a selection of the following: changing the luminance/intensity values of one or more pixels/voxels identified as being located on a determined damage; changing one or more chrominance/color values of one or more pixels/voxels identified as being located on a determined damage; changing the luminance/intensity values of one or more pixels/voxels identified as surrounding a determined damage; changing one or more chrominance/color values of one or more pixels/voxels identified as surrounding a determined damage; and/or adding an annotation, symbol or other damage indicator to the image, in connection with one or more pixels/voxels identified as being located on, or surrounding, a determined damage.

In one or more embodiments, the processor 120 may be configured to mark the determined damage to the anatomical joint in the obtained three-dimensional image representation of the anatomical joint or part of it. To mark the determined damage, the processor 120 may be configured to change the voxel value of one or more voxels on, in connection with, or surrounding a voxel identified to belong to a determined damage, such that the determined damage is visually distinguished and noticeable to a user/viewer, by performing a selection of the following: changing the luminance/intensity values of one or more voxels identified as being located on a determined damage; changing one or more chrominance/color values of one or more voxels identified as being located on a determined damage; changing the luminance/intensity values of one or more voxels identified as surrounding a determined damage; changing one or more chrominance/color values of one or more voxels identified as surrounding a determined damage; and/or adding an annotation, symbol or other damage indicator to the image, in connection with one or more voxels identified as being located on, or surrounding, a determined damage.

In one or more embodiments, the plurality of anatomical structures are anatomical structures of the knee joint, such as e.g. a selection of femur, patella, tibia, fibula, cartilage, menisci, cruciate ligaments and tendons. The plurality of anatomical structures may alternatively comprise a different selection of different parts of bone, cartilage, ligaments and/or tendons, especially if the anatomical joint is not a knee. The anatomical structures are preferably structures that are relevant to a user who uses the graphical user interface to evaluate the condition of an anatomical joint.

In one or more embodiments, a plurality of the anatomical structures is each visualized based on more than one computer file. An anatomical structure is not simply what is visualized using one computer file, but a structure that is of relevance to a user viewing and manipulating the 3D model in the graphical user interface. Many such anatomical structures are each visualized using a number of different computer files.

In one or more embodiments, the graphical user interface comprises functionality to select at least one medical image in the medical image stack to visualize through interaction with the 3D model.

In one or more embodiments, the graphical user interface comprises functionality to visualize a plurality of medical image stacks simultaneously, and functionality to visualize the position in the imaged joint of the at least one medical image from one medical image stack, that is currently visualized, in in the medical image that is visualized from the other medical image stacks.

In one or more embodiments, the processor may be configured to synchronize, or associate, the medical images and the three-dimensional image representation, so that a marking made in one of the images appear in real time in the same position in the other image. The same position is hereinafter interpreted as the same position, or same location, on the anatomical joint that is depicted.

In one or more embodiments, the medical images are MR images, and each of the plurality of medical image stacks has been generated during an MR scanning process using a specific MR sequence, and each specific MR sequence uses a unique set of MR parameters, in order to visualize different types of detail by visualizing different medical image stacks.

In one or more embodiments, the medical images are CT images, and each of the plurality of medical image stacks has been generated during an CT scanning process using a specific CT sequence, and each specific CT sequence uses a unique set of CT parameters, in order to visualize different types of detail by visualizing different medical image stacks.

The medical image stack may for example be captured during a process of scanning through different layers of the anatomical joint or part of it.

In some embodiments, the anatomical joint is a knee. In other embodiments, the anatomical joint may be any other anatomical joint suitable for damage determination using image data analysis, such as an ankle, a hip, a toe, an elbow, a shoulder, a finger or a wrist.

In one or more embodiments, the processor may be configured to select a suitable treatment from a predefined set of treatments. The selection may be based on data from the medical images and/or the three-dimensional image representation of the anatomical joint or part of it.

In some embodiments, the processor may be configured to select a suitable implant from a predefined set of implants with varying dimensions. In this context, a suitable implant means an implant having a type and dimensions that match a determined damage, thereby making it suitable for repairing the determined damage. In one or more embodiments, the processor may be configured to visualize the selected implant in the 3D model and/or the displayed medical image.

In some embodiments, the processor may be configured to propose a transfer guide tool for osteochondral autograft transplantation, possibly also including suitable size and/or suitable harvesting and/or implantation positions for at least one osteochondral autograft plug. In this context, a suitable harvesting position means a position where a suitable autograft plug can be harvested from the patient for repairing the determined damage.

In some embodiments, the graphical user interface is adapted to be used by medical staff, for example a surgeon or orthopedic staff member. The graphical user interface may then include a recommendation for a suitable treatment for repair of at least a part of the determined damage.

Alternatively, the graphical user interface includes a recommendation for a suitable design of one or more transfer guide tools for repair of at least a part of the determined damage with osteochondral autograft transplantation. The graphical user interface may in this case also include a recommendation for a suitable harvesting site for such an osteochondral autograft plug. Such suitable harvesting sites and/or transfer guide tools may further be visualized in the 3D model and/or the displayed medical image.

In some embodiments, the graphical user interface is adapted to be used by an insurance agent making an assessment regarding a client or potential client, a patient who wants to be informed about the condition of a damaged joint, or any other person who has for example a commercial or academic interest in learning about damage to a depicted anatomical joint.

The at least one manipulation tool 150 is typically configured to interpret received user input and to generate control signals in response to said received user input. The display 140 and the at least one manipulation tool 150 may be integrated in, connected to or communicatively coupled to the system 100. The at least one manipulation tool 150 may for instance be configured to interpret received user input that is being input in connection with the 3D model, and generate control signals in response to said received user input, to trigger display of an image or manipulation of image data being displayed, wherein the manipulation may be temporary or permanent. Such manipulations may for example include providing annotations, moving or changing an image or part of an image, changing the viewing perspective, zooming in or out, and/or any other suitable form of manipulation that enables the user to view and analyze the displayed image data in an improved manner. The at least one manipulation tool 150 may for example comprise a selection of a keyboard, a computer mouse, one or more buttons, touch functionality, a joystick, and/or any other suitable input device. In some embodiments, the processor 120 may be configured to receive a control signal from the at least one manipulation tool 150 and to process image data that is being displayed, or in other words manipulate a displayed image, in response to the received control signal.

The processor 120 may be configured to use a different medical image stack for obtaining the three-dimensional image representation than each of the medical image stacks used for determining damage to the identified tissue parts in the anatomical joint. In this way, the unique set of parameters used for generating each medical image stack can be optimized to the use of the medical image stack.

The processor 120 may further be configured to perform any or all of the method steps of any or all of the embodiments presented herein.

Method Embodiments

Figure 2:
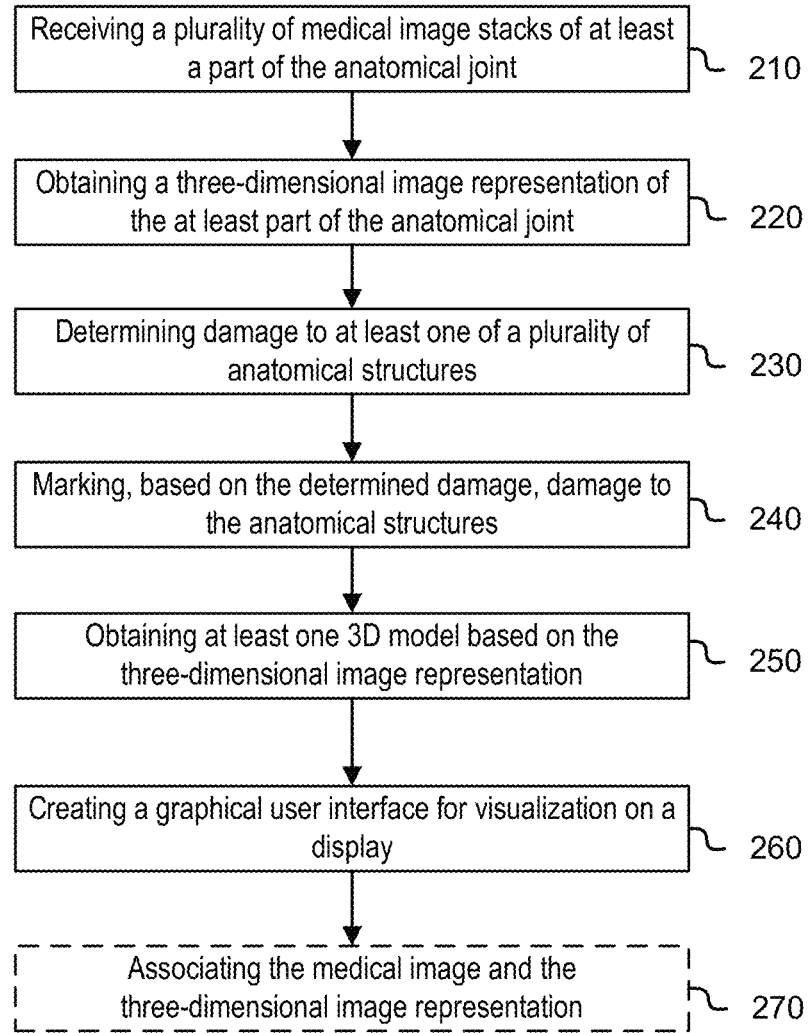
FIG. 2 is a schematic flow diagram for a method for determining and visualizing damage to at least a part of an anatomical joint, in accordance with one or more embodiments described herein.

FIG. 2 is a flow diagram of embodiments of a method for visualizing damage to an anatomical joint of a patient. In accordance with one or more to embodiments, the method 200 comprises:

In step 210: receiving a plurality of medical image stacks of at least a part of the anatomical joint.

In some embodiments, the anatomical joint is a knee. In other embodiments, the anatomical joint may be any other anatomical joint suitable for damage determination using image data analysis, such as ankle, a hip, a toe, an elbow, a shoulder, a finger or a wrist.

In step 220: obtaining a three-dimensional image representation of the at least part of the anatomical joint which is based on at least one of said medical image stacks by generating said three-dimensional image representation in an image segmentation process based on said medical image stack, or receiving said three-dimensional image representation from a storage media 110.

In step 230: determining damage to at least one of a plurality of anatomical structures in the anatomical joint by analyzing at least one of the plurality of medical image stacks.

In step 240: marking, based on the determined damage, damage to the anatomical structures in the obtained three-dimensional image representation.

In step 250: obtaining at least one 3D model based on the three-dimensional image representation, in which 3D model the marked damage is visualized. The 3D model may essentially correspond to the three-dimensional image representation, or be a processed version of the three-dimensional image representation.

In step 260: creating a graphical user interface for visualization on a display, the graphical user interface comprising: functionality to visualize and enable manipulation, using at least one manipulation tool, of the at least one 3D model; functionality to enable removal of the visualization of at least one of the plurality of anatomical structures from the at least one 3D model; functionality to visualize and enable browsing of at least one of the plurality of medical image stacks; and functionality to, in the 3D model, visualize the position of the at least one medical image that is currently visualized.

In one or more embodiments, the marking of method step 240 may include changing the pixel/voxel value of one or more pixels/voxels on, in connection with, or surrounding a pixel/voxel identified to belong to a determined damage, such that the determined damage is visually distinguished and noticeable to a user/viewer. Such a change of pixel/voxel values of one or more pixels/voxels on, in connection with, or surrounding a pixel/voxel identified to belong to a determined damage may for example comprise a selection of the following: changing the luminance/intensity values of one or more pixels/voxels identified as being located on a determined damage; changing one or more chrominance/color values of one or more pixels/voxels identified as being located on a determined damage; changing the luminance/intensity values of one or more pixels/voxels identified as surrounding a determined damage; changing one or more chrominance/color values of one or more pixels/voxels identified as surrounding a determined damage; and/or adding an annotation, symbol or other damage indicator to the image, in connection with one or more pixels/voxels identified as being located on, or surrounding, a determined damage.

Some or all of the anatomical structures may each be visualized based on more than one computer file. An anatomical structure is not simply what is visualized using one computer file, but a structure that is of relevance to a user viewing and manipulating the 3D model in the graphical user interface. Many such anatomical structures are each visualized using a number of different computer files.

In embodiments, the plurality of anatomical structures are anatomical structures of the knee joint, such as e.g. a selection of femur, patella, tibia, fibula, cartilage, menisci, cruciate ligaments and tendons. The plurality of anatomical structures may alternatively comprise a different selection of different parts of bone, cartilage, ligaments and/or tendons, especially if the anatomical joint is not a knee. The anatomical structures are preferably structures that are relevant to a user who uses the graphical user interface to evaluate the condition of an anatomical joint.

In embodiments, the graphical user interface comprises functionality to functionality to select at least one medical image in the medical image stack to visualize through interaction with the 3D model.

In embodiments, the graphical user interface comprises functionality to visualize a plurality of medical image stacks simultaneously, and functionality to visualize the position in the imaged joint of the at least one medical image from one medical image stack, that is currently visualized, in in the medical image that is visualized from the other medical image stacks.

In some embodiments, the medical images are MR images, and each of the plurality of medical image stacks has been generated during an MR scanning process using a specific MR sequence, wherein each specific MR sequence uses a unique set of MR parameters, in order to visualize different types of detail by visualizing different medical image stacks.

In other embodiments, the medical images are CT images, and each of the plurality of medical image stacks has been generated during a CT scanning process using a specific CT sequence, wherein each specific CT sequence uses a unique set of CT parameters, in order to visualize different types of detail by visualizing different medical image stacks.

In some embodiments, medical images and the three-dimensional image representation may be associated, or synchronized, so that a marking made in one of the images appears in the same position in the other image.

The method may thus further comprise:

In step 270: Associating the medical image and the three-dimensional image representation, so that a marking made in one of the images appear in the same position in the other image.

Figure 3:
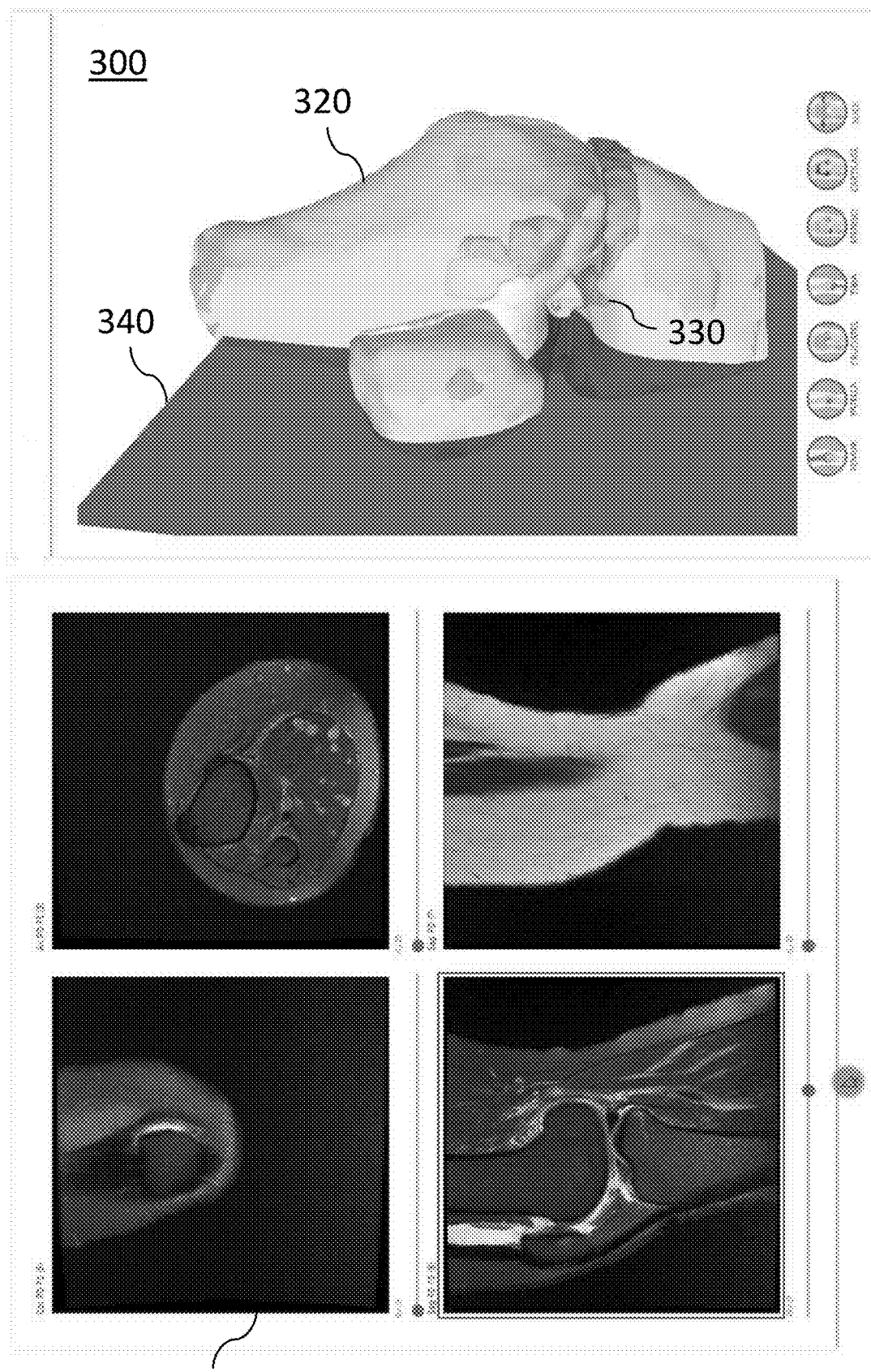
FIG. 3 shows an example of a graphical user interface for determining and visualizing damage to an anatomical joint, in accordance with one or more embodiments described herein.

FIG. 3 shows an example of a graphical user interface 300 comprising four displayed medical images 310 and a 3D model 320 in which determined damage 330 to an anatomical joint is visualized, in accordance with one or more embodiments described herein. The determined damage 330 may e.g. be visualized by changing the luminance/intensity levels and/or chrominance/color values of a number of pixels/voxels identified as being located on and surrounding the determined damage. Of course, any luminance/intensity values and/or chrominance/color values may be chosen, depending on the application, and depending on what provides a clear marking, visualization, or indication that enables a person viewing the graphical user interface to see and analyze the determined damage. A chosen luminance/intensity value and/or chrominance/color value may in embodiments be assigned to a pixel/voxel by replacing the previous pixel/voxel value, or by blending the new pixel/voxel values with the old pixel/voxel value using a scaling factor, such as an alpha blending factor. Determined damage may further be visualized using different assigned pixel/voxel values depending on the type of damage that each pixel represents. As an example, visualizing a damage may comprise different new pixel/voxel values for: a full-depth damage, i.e. a cartilage damage down to the bone; a partial depth damage, such as degenerated cartilage, regenerated cartilage/scar tissue, or deformed cartilage; a bone marrow lesion (BML); and a distinct cyst.

The graphical user interface may comprise functionality to visualize and enable manipulation, using the at least one manipulation tool, of the at least one 3D model 320. The graphical user interface may further comprise functionality to visualize and enable browsing of at least one of the plurality of medical image stacks. In the graphical user interface illustrated in FIGS. 3-5, four image stacks are visualized. Below each of these image stacks, an indicator shows the position within the image stack of the image that is currently displayed. In the image to the bottom left in FIG. 3, the indicator shows that the user is browsing through the medical image stack. The position of the image in the medical image stack that is currently visualized, i.e. the intersection in the 3D model that is displayed in the medical image 310, is in FIG. 3 illustrated with a plane 340 through the 3D model. As the user browses through the medical images, the plane 340 moves in the 3D model 320.

Figure 4:
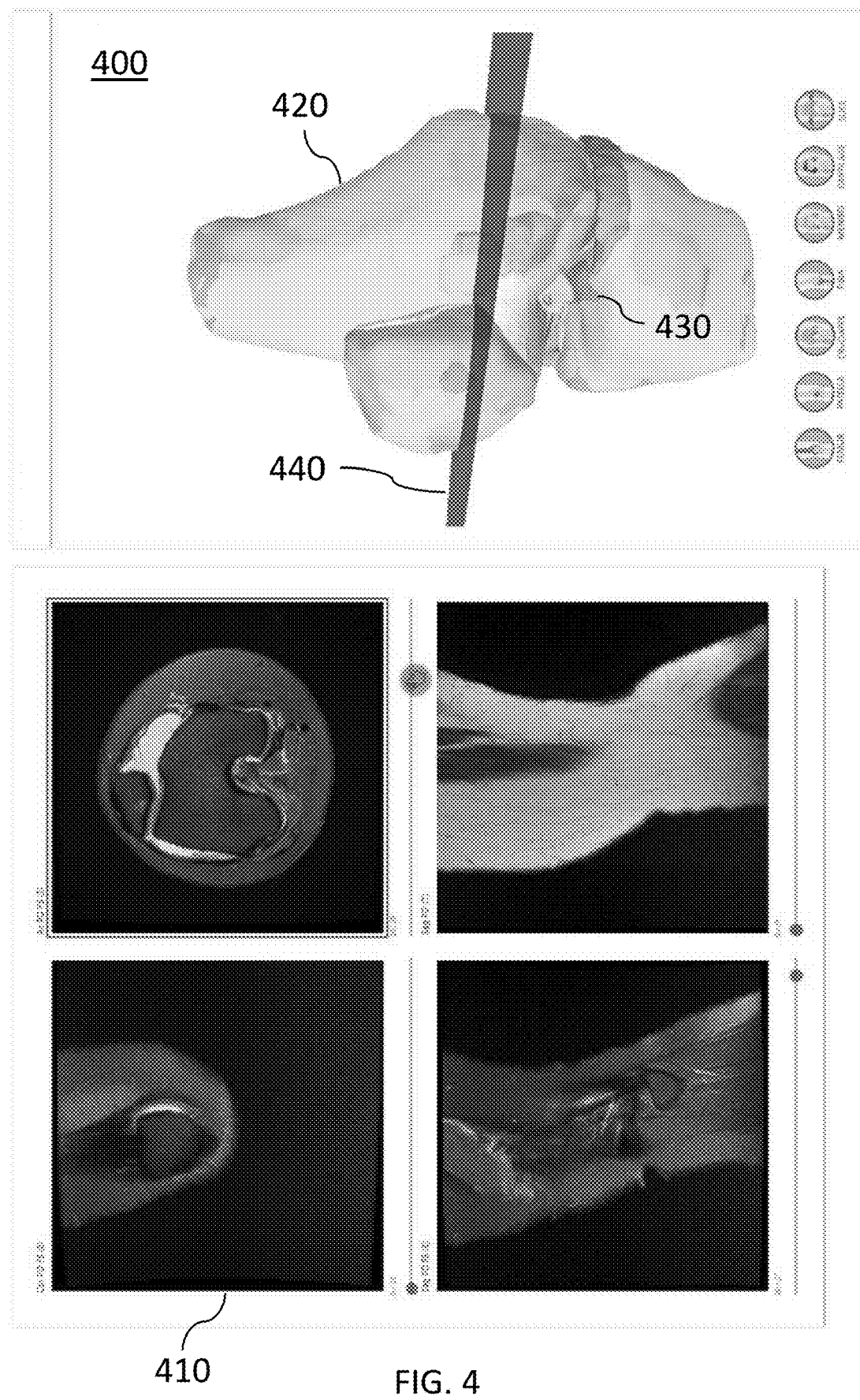
FIG. 4 shows an example of a graphical user interface for determining and visualizing damage to an anatomical joint, in accordance with one or more embodiments described herein.

FIG. 4 illustrates that the angle of such a plane 440 depends on the angle of the slices visualized in the images in the medical image stack, and the plane 340, 440 may thus be at any angle through the 3D model. The user preferably has the option to remove the visualization of this plane 340, 440, for increased clarity when viewing the 3D model.

The graphical user interface may further comprise functionality to enable removal of the visualization of at least one of the plurality of anatomical structures from the at least one 3D model. In the graphical user interface illustrated in FIGS. 3-5, the following anatomical structures are represented by "buttons" which may be manipulated using the at least one manipulation tool: femur, patella, cruciates, tibia, menisci and cartilage. Using these "buttons", these anatomical structures may be selectively added and removed from the visualization of the 3D model, as illustrated in FIG. 5.

The graphical user interface may further comprise functionality to select at least one medical image 310, 410, 510 in the medical image stack to visualize through interaction with the 3D model 320, 420, 520, e.g. by manipulating the plane through the 3D model 320, 420, 520 using the at least one manipulation tool.

Figure 5:
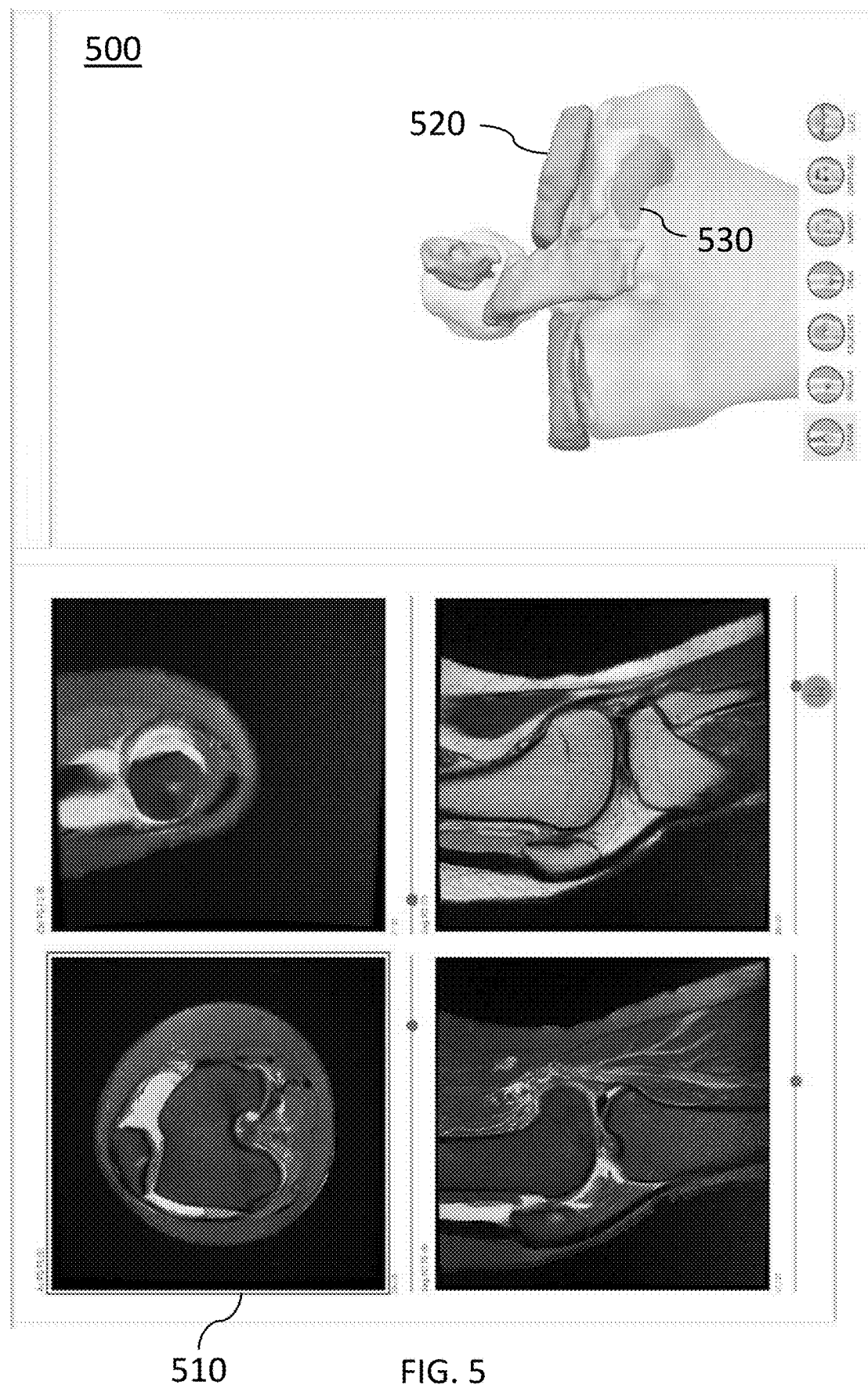
FIG. 5 shows an example of a graphical user interface for determining and visualizing damage to an anatomical joint, in accordance with one or more embodiments described herein.

In FIGS. 3-5, a plurality of medical images 310, 410, 510 are shown. The plurality of medical images 310, 410, 510 may e.g. belong to different medical image stacks. In this way, the graphical user interface may comprise functionality to browse through a number of different medical image stacks.

In some embodiments, the graphical user interface may further include a recommendation and/or a position indication of a suitable implant for the determined bone and/or cartilage damage. Such a suitable implant may further be visualized in the 3D model and/or the displayed medical image.

Figure 6:
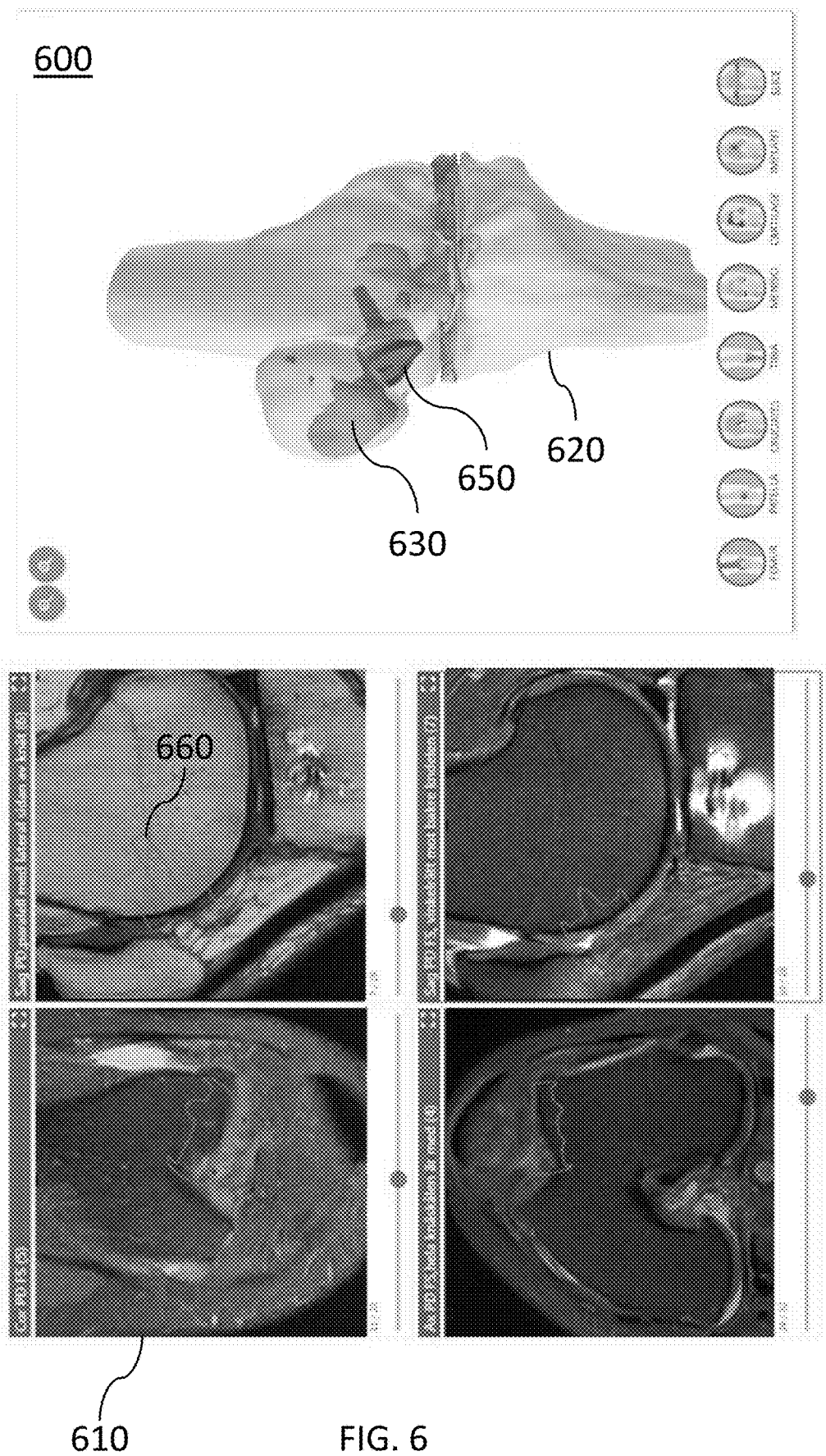
FIG. 6 shows an example of a graphical user interface for determining and visualizing damage to an anatomical joint, in accordance with one or more embodiments described herein.

An example of how or a type and placement of a suitable implant may be indicated in the graphical user interface is shown in FIG. 6, which comprises four displayed medical images 610 and a 3D model 620. The type and placement of a suitable implant 650, 660 is in FIG. 6 indicated both in the in the medical image 610 and in the 3D model 620, but it may be indicated in just the 3D model 620.

In one or more embodiments, the graphical user interface is adapted to be used by medical staff, for example a surgeon or orthopedic staff member. In one or more embodiments, the graphical user interface is adapted to be used by medical staff, for example a surgeon or orthopedic staff member, and may further include a recommendation for a suitable implant, according to any of the embodiments described above.

In some embodiments, the graphical user interface is adapted to be used by an insurance agent making an assessment regarding a client or potential client, a patient who wants to be informed about the condition of a damaged joint, or any other person who has for example a commercial or academic interest in learning about damage to a depicted anatomical joint.

Figure 7:
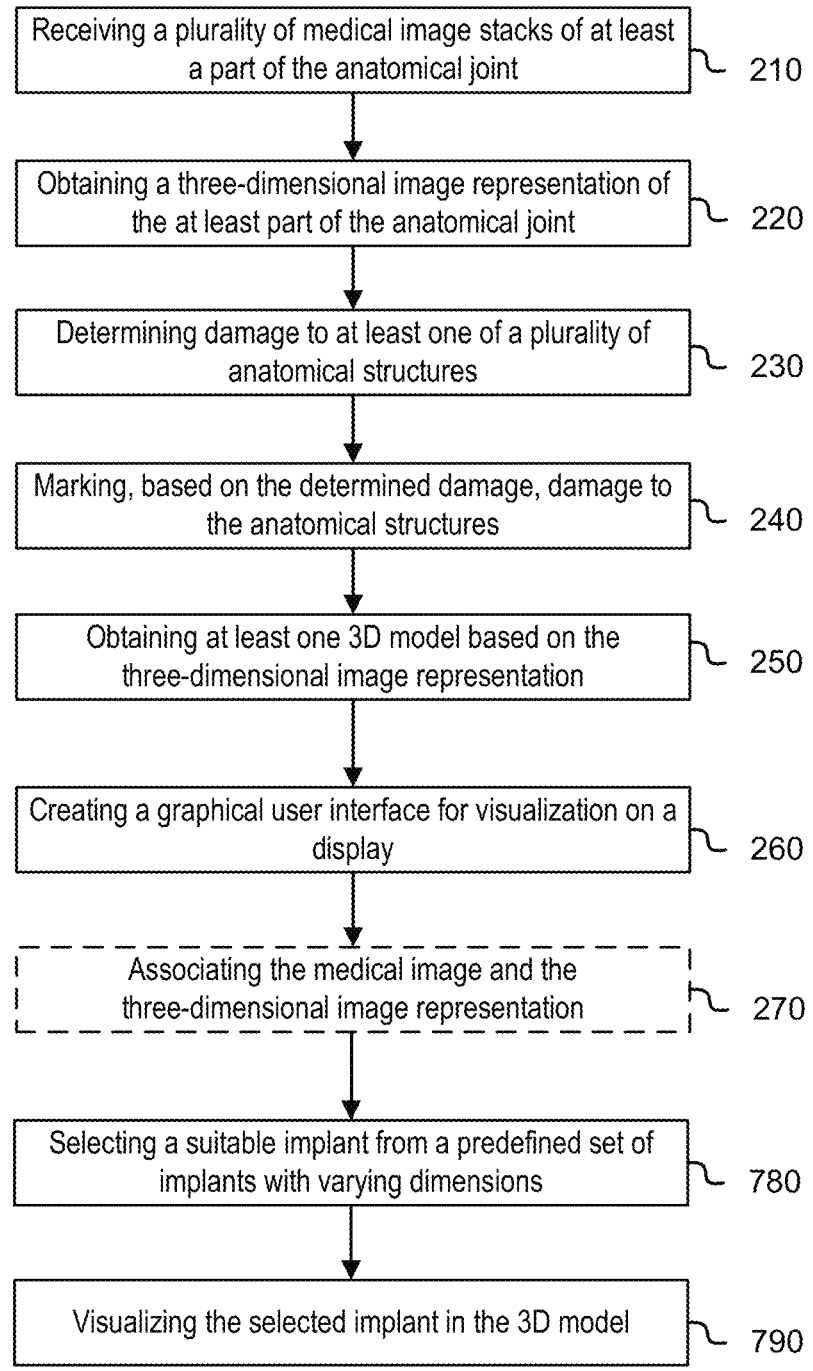
FIG. 7 is a schematic flow diagram for a method for determining and visualizing damage to at least a part of an anatomical joint, in accordance with one or more embodiments described herein.

FIG. 7 is a flow diagram of one or more method embodiments for determining and visualizing damage to an anatomical joint of a patient where damage to the joint is visualized in a graphical user interface, and further the optional method steps of including in the images a recommendation of a suitable implant for repairing a determined damage. Steps 210-270 of FIG. 7 correspond to the same steps of FIG. 2, and the method embodiments of FIG. 7 further comprise the following additional steps:

In step 780: selecting a suitable implant from a predefined set of implants with varying dimensions, based on data from the medical image and/or the three-dimensional image representation of the anatomical joint or part of it.

In this context, a suitable implant means an implant having a type and dimensions that match a determined damage, thereby making it suitable for repairing the determined damage.

In step 790: visualizing the selected implant in the 3D model.

In one or more embodiments, the graphical user interface may be manipulated by a user using at least one manipulation tool integrated in, connected to, or communicatively coupled to the display or a system comprising the display. According to these embodiments, the method of FIG. 2 or 7 may further optionally comprise receiving user input from at least one manipulation tool, interpret the received user input, and generate one or more control signals in response to the received user input. The received user input may e.g. relate to the 3D model, and generate control signals in response to said received user input to manipulate what is being displayed, temporarily or permanently. The manipulation may for example include providing annotations, moving or changing an image or part of an image, changing the viewing perspective, zooming in or out, and/or any other suitable form of manipulation that enables the user to view and analyze the displayed image data in an improved manner. In some embodiments, the method of FIG. 2 or 7 may comprise receiving a control signal from at least one manipulation tool and processing the image data that is being displayed, or in other words manipulate the displayed image, in response to the control signal.

Each of the medical image stacks used for determining damage to the identified tissue parts in the anatomical joint may be different from the medical image stack used for obtaining the three-dimensional image representation. In this way, the unique set of parameters used for generating each medical image stack can be optimized to the use of the medical image stack.

The method may further comprise marking, in the 3D model, the position of the displayed medical image. This makes it easier for the user to determine what is shown in the displayed medical image.

The functionality to browse the medical image stack may also comprise functionality to select a medical image in the medical image stack through interaction with the 3D model. This is an easy way for the user to visualize interesting parts of the joint.

Any or all of the method steps of any or all of the embodiments presented herein may be performed automatically, e.g. by at least one processor.

Use Case Embodiment

To set the presently disclosed methods and systems in a larger context, the damage marking and the creation of the graphical user interface according to any of the disclosed embodiments may in use case embodiments be preceded by capturing and/or obtaining medical image data representing an anatomical joint or part of it, and may further be followed by actions to be taken in view of repairing any determined damage.

Figure 8:
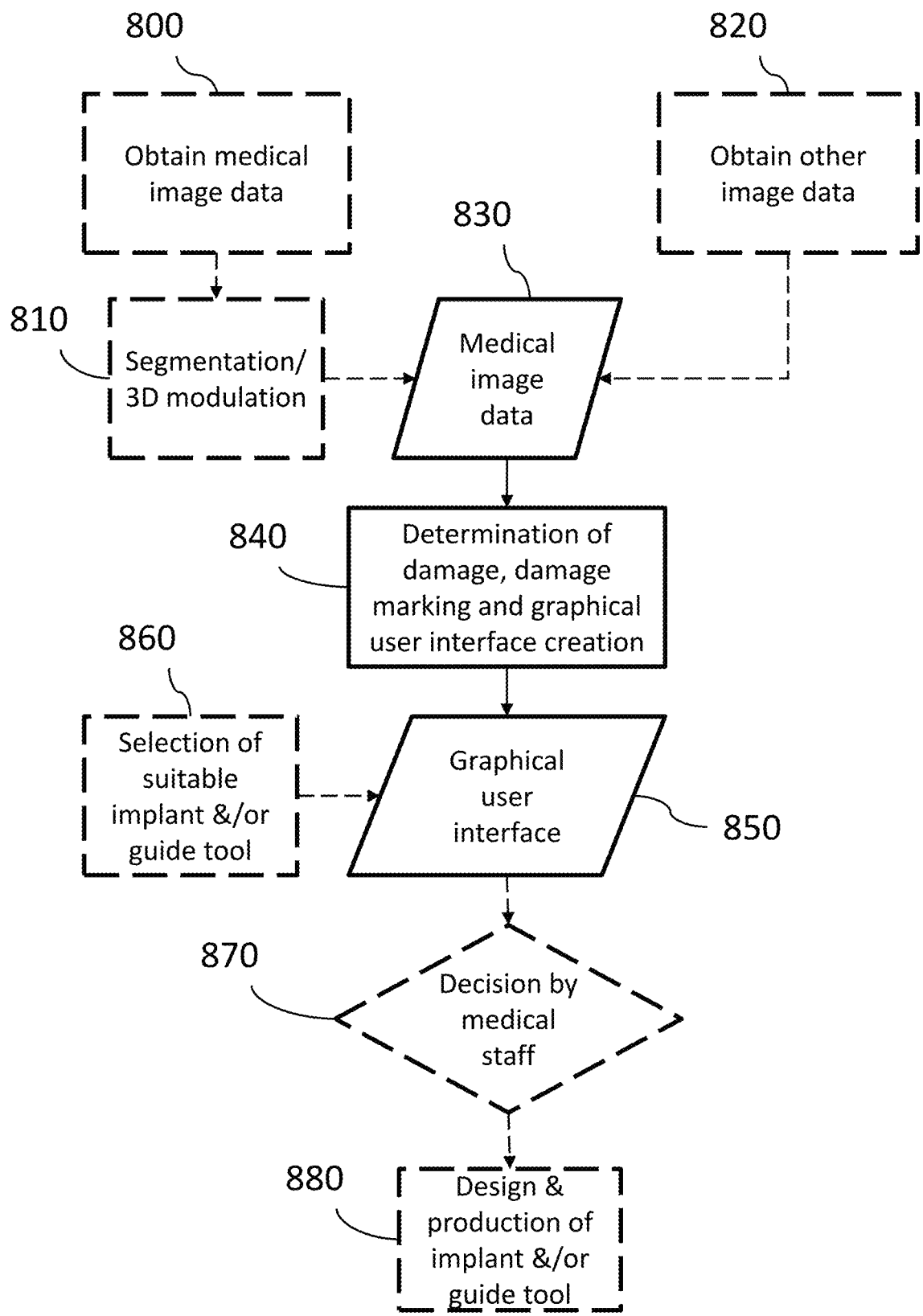
FIG. 8 is a flow diagram exemplifying the steps from obtaining medical image data to designing and producing an implant and/or guide tool for repair of a determined damage to an anatomical joint, including the steps of damage marking and creation of a graphical user interface to visualize damage to an anatomical joint of a patient, in accordance with one or more embodiments described herein.

FIG. 8 is a flow diagram exemplifying one such larger context, including obtaining medical image data from an image source, determining damage to a depicted anatomical joint, and creating of a graphical user interface in accordance with one or more embodiments described herein. FIG. 8 further includes steps of designing and producing an implant and/or guide tool suitable for repairing a determined damage in an anatomical joint. In FIG. 8, everything except the determination of damage, damage marking and graphical user interface creation of step 840, using the input medical image data 830 and resulting in the output graphical user interface 850, is marked with dashed lines to clarify they are optional steps shown in the figure to provide context only, and not essential to any of the embodiments presented herein. Especially, steps 870 and 880 relating to diagnosis/decision on treatment and design and production of implant/guide tool are not part of the embodiments presented herein.

According to the example shown in FIG. 8, medical image data 830 may be obtained in a step 800 in the form of medical image data from a medical imaging system. The medical image data obtained may for example be radiology data, generated using one or more of a variety of medical imaging techniques such as X-ray images, ultrasound images, computed tomography (CT) images, nuclear medicine including positron emission tomography (PET) images, and magnetic resonance imaging (MRI) images. The medical image data may e.g. be captured during a process of scanning images through different layers of the anatomical joint or part of it.

Each medical image stack may e.g. have been generated during a scanning process using a specific sequence, where each specific sequence uses a unique set of parameters. Such a scanning process may be any type of scanning process for generating a series of radiology images where different sets of parameters may be used to generate images with different types of detail. The use of more than sequence allows the visualization of more detail in the image, since some types of detail may be more clearly visible using one set of parameters and other types of detail may be more clearly visible using another set of parameters.

The scanning processes used for generating the medical image stacks may e.g. be MR scanning process using different specific MR sequences, where each MR sequence uses a unique set of MR parameters. The MR parameters may e.g. be the repetition time TR (the time between the RF pulses) and the echo time TE (the time between an RF pulse and its echo). Depending on the desired information, the set of MR parameters may e.g. cause a T1 weighted MR sequence if a short TR and a short TE is selected, a T2 weighted MR sequence if a long TR and a long TE is selected, or an intermediately weighted MR sequence of a long TR and a short TE is selected. The different sets of MR parameters do not necessarily have to cause MR sequences of different types—two different sets of MR parameters may e.g. both cause T1 weighted sequences, but one of the sets may cause a stronger T1 weighting than the other. There are also other MR parameters, such as e.g. flip angle, bandwidth or different types of fat suppression or enhancement of gadolinium, which may be varied between the MR sequences. It may be advantageous to use very different sets of MR parameters for generating the medical image stack used for generating the 3D model and for generating the other medical image stacks. It may e.g. be advantageous to use a specific 3D MRI sequence for generating the medical image stack used for generating the 3D model.

The scanning processes used for generating the medical image stacks may also be CT scanning processes using different specific CT sequences, where each CT sequence uses a unique set of CT parameters. The CT parameters may e.g. be the tube potential (kV), the tube current (mA), the tube current product (mAs), the effective tube current-time product (mAs/slice), the tube current modulation (TCM), the table feed per rotation (pitch), the detector configuration, the collimation, the reconstruction algorithm, the patient positioning, the scan range and/or the reconstructed slice thickness. Also in CT scanning, it may be advantageous to use very different sets of CT parameters for generating the medical image stack used for generating the 3D model and for generating the other medical image stacks.

The image data obtained in step 800 may further be processed in a step 810, by performing segmentation and 3D modulation to obtain a three-dimensional image representation of what is depicted in the captured image data. For instance, if the image data captured depict an anatomical joint, the three-dimensional image representation would be a three-dimensional image representation of the anatomical joint. Medical images may also be obtained in a step 820 from a different kind of image source that provides medical images. The three-dimensional image representation and the medical images both depict the same object, namely the anatomical joint of interest for damage determination. The medical image data 830 may therefore, as described herein, comprise a three-dimensional image representation and/or medical images representing an anatomical joint. The medical image data 830 may represent only a part of the anatomical joint.

The three-dimensional image representation and the medical images may in embodiments be associated, or synchronized, such that a position on an object depicted in the three-dimensional image representation is associated with the same position on the same object in the medical images. Thereby, if a marking of a determined damage is done in the three-dimensional image representation, it will appear in the same position on the depicted anatomical joint in the medical images, and vice versa. Of course, once the three-dimensional image representation and the medical images have been associated, or synchronized, the same would apply to for example annotations placed in connection with a position of the depicted joint, or any modification done to the three-dimensional image representation or the medical images.

In a step 840, damage determination, marking of damage in the input medical image data 830 and creation of the output graphical user interface 850 is performed, in accordance with any of the embodiments presented herein in connection with the method and system descriptions. The graphical user interface 850 may, in accordance with embodiments described herein, comprise functionality to visualize and enable manipulation, using the at least one manipulation tool, of at least one 3D model; functionality to enable removal of the visualization of at least one of a plurality of anatomical structures from the at least one 3D model; functionality to visualize and enable browsing of at least one of a plurality of medical image stacks; functionality to select at least one medical image in the medical image stack to visualize through interaction with the 3D model; and functionality to visualize, in the 3D model, the position of the at least one medical image that is currently visualized. The graphical user interface 850 may optionally, in accordance with embodiments described herein, comprise an indication of one or more suitable implants and/or guide tools that may be used for repairing a determined damage. In this context, a suitable implant and/or guide tool means an implant and/or guide tool having a type and dimensions that match the determined damage, thereby making it suitable for repairing the determined damage. The one or more suitable implants and/or guide tools may be selected in the optional step 860, and may be presented graphically in connection with the 3D model and/or the medical images of the graphical user interface 850, for example in the position where the implant and/or guide tool should optimally be inserted to repair the determined damage. Alternatively, the one or more suitable implants and/or guide tools may be selected in the optional step 860 and may be presented separated from the 3D model and/or the medical images, for example as a graphical representation and/or a text annotation.

In a use case embodiment, a medical staff member, for example a surgeon or orthopedic staff member, may use a created graphical user interface 850 to make a correct diagnosis and make a decision 870 on an decision of optimal treatment of the patient whose anatomical joint has been depicted. If the medical staff member decides that an implant is required, this may lead up to the step 880 of designing and producing a suitable implant and/or guide tool, possible according to an indication that may be provided in the graphical user interface, as described herein, for repairing the determined damage.

In another use case embodiment, a person using the graphical user interface 850 may be a person other than a medical staff member that has an interest in learning about any damage to the depicted anatomical joint, for example an insurance agent assessing a client or a potential client, a patient who wants to be informed about the condition of a damaged joint, or any other person who has for example a commercial or academic an interest in learning about any damage to a depicted anatomical joint.

Further Embodiments

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the claimed scope of the present disclosure. Where applicable, the various hardware components and/or software components set forth herein can be separated into sub-components comprising software, hardware, or both without departing from the claimed scope of the present disclosure. In addition, where applicable, it is contemplated that software components can be implemented as hardware components, and vice-versa. The method steps of one or more embodiments described herein may be performed automatically, by any suitable processing unit, or one or more steps may be performed manually. Where applicable, the ordering of various steps described herein can be changed, combined into composite steps, and/or separated into sub-steps to provide features described herein.

Software in accordance with the present disclosure, such as program code and/or data, can be stored in non-transitory form on one or more machine-readable mediums. It is also contemplated that software identified herein can be implemented using one or more general purpose or specific purpose computers and/or computer systems, networked and/or otherwise.

In embodiments, there are provided a computer program product comprising computer readable code configured to, when executed in a processor, perform any or all of the method steps described herein. In some embodiments, there are provided a non-transitory computer readable memory on which is stored computer readable and computer executable code configured to, when executed in a processor, perform any or all of the method steps described herein.

In one or more embodiments, there is provided a non-transitory machine-readable medium on which is stored machine-readable code which, when executed by a processor, controls the processor to perform the method of any or all of the method embodiments presented herein.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Accordingly, the scope of the invention is defined only by the claims.

All references including publications, patent applications, and patents cited herein are hereby incorporated by reference to the same extent as if each reference were individually and specifically indicated to be incorporated by reference and were set forth in its entirety herein.

The invention claimed is:

1. System for determining and visualizing damage to an anatomical joint of a patient, the system comprising a display, at least one manipulation tool, a storage media and at least one processor, wherein the at least one processor is configured to:
   i) receive a plurality of medical image stacks of at least part of the anatomical joint from the storage media;
   ii) obtain a three-dimensional (3D) image representation of the at least part of the anatomical joint which is based on at least one of said medical image stacks, by generating said three-dimensional image representation in an image segmentation process based on said medical image stack, or receiving said three-dimensional image representation from the storage media;
   iii) determine damage to at least one of a plurality of anatomical structures in the anatomical joint by analyzing at least one of said plurality of medical image stacks;
   iv) mark, based on the determined damage, damage to the anatomical structures in the obtained three-dimensional image representation;
   v) obtain at least one 3D model for visualization based on the three-dimensional image representation, the 3D model comprising information that models the determined damage to allow visualization of the marked damage; and
   vi) create a graphical user interface for visualization on the display of the anatomical joint and the marked damage, the graphical user interface comprising:
      functionality to visualize the marked damage and enable manipulation, using the at least one manipulation tool, of the at least one 3D model; and
      functionality to enable selective removal of at least one of the plurality of anatomical structures from the visualization of the at least one 3D model, the functionality implemented by at least a plurality of user interface elements each corresponding to a respective anatomical structure to enable a user to interact with a user interface element of the plurality of user interface elements to cause a corresponding anatomical structure to be removed from the visualization to increase clarity when viewing the marked damage.

2. System according to claim 1, wherein the plurality of anatomical structures comprises anatomical structures of a knee joint selected from the group consisting of femur, patella, tibia, fibula, cartilage, menisci, cruciate ligaments, and tendons.

3. System according to claim 1, wherein a plurality of the anatomical structures is each visualized based on more than one computer file.

4. System according to claim 1, wherein the medical images are magnetic resonance (MR) images, and each of the plurality of medical image stacks has been generated during an MR scanning process using a specific MR sequence, wherein each specific MR sequence uses a unique set of MR parameters, in order to visualize different types of detail by visualizing different medical image stacks.

5. System according to claim 1, wherein the medical images are computed tomography (CT) images, and each of the plurality of medical image stacks has been generated during a CT scanning process using a specific CT sequence, wherein each specific CT sequence uses a unique set of CT parameters, in order to visualize different types of detail by visualizing different medical image stacks.

6. System according to claim 1, wherein the graphical user interface provides a first identifier for a first anatomical feature and a second identifier of a second anatomical feature to enable selection of the visualization of the at least one of the plurality of anatomical structures to be removed.

7. Method for determining and visualizing damage to an anatomical joint of a patient, the method comprising the steps of:
   i) receiving a plurality of medical image stacks of at least part of the anatomical joint;
   ii) obtaining a three-dimensional image representation of the at least part of the anatomical joint which is based on at least one of said medical image stacks, by generating said three-dimensional (3D) image representation in an image segmentation process based on said medical image stack, or receiving said three-dimensional image representation from a storage media;
iii) determining damage to at least one of a plurality of anatomical structures in the anatomical joint by analyzing at least one of said plurality of medical image stacks;
iv) marking, based on the determined damage, damage to the anatomical structures in the obtained three-dimensional image representation;
v) obtaining at least one 3D model based on the three-dimensional image representation, the 3D model comprising information to model the determined damage to enable visualization of the marked damage; and
vi) creating a graphical user interface for visualization on a display of the anatomical joint and the marked damage, the graphical user interface comprising:
functionality to visualize the marked damage and enable manipulation, using at least one manipulation tool, of the at least one 3D model; and
functionality to enable selective removal of at least one of the plurality of anatomical structures from the visualization of the at least one 3D model, the functionality comprising a first user interface element with which interaction causes removal of a first anatomical structure from the visualization and comprising a second user interface element with which interaction causes removal of a corresponding second anatomical structure to increase clarity when viewing the marked damage.

8. Method according to claim 7, wherein the plurality of anatomical structures comprise one or more of femur, patella, tibia, fibula, cartilage, menisci, cruciate ligaments, or tendons.

9. Method according to claim 7, wherein a plurality of the anatomical structures is each visualized based on more than one computer file.

10. Method according to claim 7, wherein the medical images are magnetic resonance (MR) images, and each of the plurality of medical image stacks has been generated during an MR scanning process using a specific MR sequence, wherein each specific MR sequence uses a unique set of MR parameters, in order to visualize different types of detail by visualizing different medical image stacks.

11. Method according to claim 7, wherein the medical images are computed tomography (CT) images, and each of the plurality of medical image stacks has been generated during a CT scanning process using a specific CT sequence, wherein each specific CT sequence uses a unique set of CT parameters, in order to visualize different types of detail by visualizing different medical image stacks.

12. Method according to claim 7, wherein the graphical user interface enables selection of anatomical features to be added to the visualization of the 3D model.

* * * * *